United States Patent [19]

Wolff et al.

[11] 4,153,728

[45] May 8, 1979

[54] PHENOXYALKYLCARBOXYLIC ACID COMPOUNDS AND THERAPEUTIC COMPOSITIONS

[75] Inventors: Hans P. Wolff, Mannheim; Ernst-Christian Witte, Mannheim; Max Thiel, Mannheim; Harald Stork, Mannheim-Feudenheim; Egon Roesch, Mannheim, all of Fed. Rep. of Germany

[73] Assignee: Boehringer Mannheim GmbH, Mannheim, Fed. Rep. of Germany

[21] Appl. No.: 733,542

[22] Filed: Oct. 18, 1976

[30] Foreign Application Priority Data

Oct. 21, 1975 [DE] Fed. Rep. of Germany ....... 2546996

[51] Int. Cl.² .................. C07C 101/42; A01N 9/20
[52] U.S. Cl. .................. 424/319; 424/309; 560/42; 562/451; 260/501.11
[58] Field of Search ............ 260/471 R, 519, 471; 424/308, 309, 319; 560/42; 562/451

[56] References Cited

U.S. PATENT DOCUMENTS

| | | | |
|---|---|---|---|
| 3,398,187 | 8/1968 | Drain | 260/519 |
| 3,781,328 | 12/1973 | Witte et al. | 260/471 R |
| 4,010,279 | 3/1977 | Griss et al. | 260/471 R |
| 4,026,896 | 5/1977 | Harita et al. | 424/319 |

Primary Examiner—James O. Thomas, Jr.
Assistant Examiner—James H. Reamer
Attorney, Agent, or Firm—Sprung, Felfe, Horn, Lynch & Kramer

[57] ABSTRACT

Novel phenoxyalkylcarboxylic acid compounds of the formula

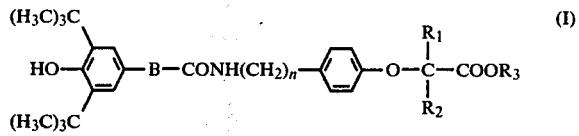

wherein
B is a valency bond or a straight-chained or branched, saturated or unsaturated hydrocarbon radical containing up to 3 carbon atoms;
n is 1 or 2 and
$R_1$, $R_2$ and $R_3$ are hydrogen or lower alkyl; and the pharmacologically compatible salts thereof; have been found to be outstandingly effective in lowering the serum lipid level and the cholesterol level in mammals without inducing undesired side effects and to possess excellent thrombocyte-aggregation inhibiting activity.

18 Claims, No Drawings

PHENOXYALKYLCARBOXYLIC ACID COMPOUNDS AND THERAPEUTIC COMPOSITIONS

The present invention is concerned with new phenoxyalkylcarboxylic acid compounds and to therapeutic compositions and methods containing and utilizing such compounds.

The new phenoxyalkylcarboxylic acid derivatives of the present invention are of the formula:

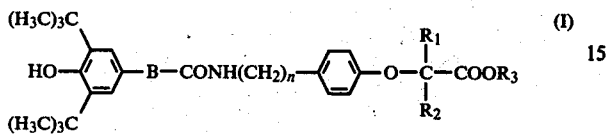

wherein

B is a valency bond or a straight-chained or branched, saturated or unsaturated hydrocarbon radical containing up to 3 carbon atoms, n is 1 or 2 and $R_1$, $R_2$ and $R_3$, which can be the same or different, are hydrogen atoms or lower alkyl; and the pharmacologically compatible salts thereof.

Examples of straight-chained or branched, saturated or unsaturated hydrocarbon radicals containing up to 3 carbon atoms which are represented by B include alkylene, such as methylene, methylmethylene, dimethylmethylene and ethylene; and alkenylene, such as vinylene.

The lower alkyl radicals $R_1$, $R_2$ and $R_3$ can be straight chained or branched and contain up to 6 and preferably up to 3 carbon atoms.

The above-given definitions of the compounds according to the present invention are also to include all possible stereoisomers, as well as mixtures thereof.

The new compounds according to the present invention, as well as their pharmacologically compatible salts, show, in animal experiments, a considerable lowering of the serum lipid level and of the cholesterol level, without undesirable side effects. The new compounds according to the present invention and the salts thereof are, therefore, effective agents for the treatment of atherosclerosis. Furthermore, they possess an outstanding thrombocyte aggregation-inhibiting action. In addition, they can be used for the inhibition of the growth of tumors and retard the ageing of cells. Furthermore, they are also valuable intermediates for the preparation of antibiotics with a β-lactam structure.

The new compounds according to the present invention can be prepared by reacting an aminophenol of the general formula:

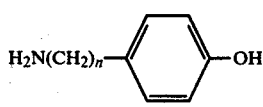

in which n has the same meaning as above, optionally with the intermediate protection of the amino or hydroxyl group, in any order with an acid of the general formula:

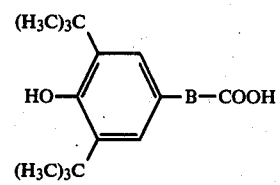

in which B has the same meaning as above, or with a derivative thereof, and with a compound of the general formula:

in which $R_1$ and $R_2$ have the same meanings as above, X is a reactive group and Y is a —$COOR_3$ group, in which $R_3$ has the same meaning as above or Y is a residue which, after condensation has taken place, is converted into a —$COOR_3$ group, whereafter, if desired, the substituent $R_3$ in the product obtained is, after the condensation, converted in known manner into another substituent $R_3$ and the compound obtained is, if desired, converted into a pharmacologically compatible salt.

The process according to the present invention is preferably carried out in two stages. The condensation of the compounds of general formula (II) with derivatives of the carboxylic acids (III), on the one hand, and with compounds of the general formula (IV), on the other hand, is preferably carried out in such a manner that, first, one of the two reactive groups of the compounds (II) is blocked by a protective group which is easily split off, the compound obtained is reacted with a derivative of a carboxylic acid (III) or with a compound of general formula (IV), the protective group is again removed and subsequently this reactive intermediate is reacted with the hitherto unused compound of general formula (IV) or (III).

The reactive derivatives of the carboxylic acids (III) are preferably the halides, anhydrides, the mixed carboxylic acid-carbonic acid anhydrides or the imidazolides. These can be reacted, for example, under the conditions of a Schotten-Baumann reaction, i.e. with the addition of a tertiary amine, such as pyridine, dimethylaniline or triethylamine, with the compound (II) in an inert solvent, for example, tetrahydrofuran, dioxan or an excess of the tertiary amine. A previous blocking of the phenolic hydroxyl group by esterification is preferred but etherification with a compound of general formula (IV) is especially preferred. On the other hand, a reactive derivative of a compound (II) can be reacted with a carboxylic acid of general formula (III). Reactive derivatives of compounds (II) include, for example, the phosphoazoamides, which are formed in situ when a phosphorus trihalide, such as phosphorus trichloride, is added to a solution of the compound (II) protected on the hydroxyl group. As solvent and simultaneously as acid acceptor, there can be used a tertiary amine, for example pyridine. If this reaction is carried out in the presence of a carboxylic acid, then the desired amides with a protected hydroxyl function are obtained directly.

For the reaction of the compound (II) with a compound (IV), it has proved to be advantageous first to convert the amino group of the compound (II) into a protected group, for example a phthalimide group, which, after the reaction, can easily be split off again, for example by reaction with hydroxylamine. However, there can also be introduced other groups known from peptide chemistry for the protection of the amine group which, after the reaction, are split off again. The amino group is preferably blocked with an acyl group, such as a formyl or acetyl group, which, after the reaction, can easily be split off again with a strong base, for example sodium hydroxide or potassium hydroxide.

As reactive compounds (IV), those are especially preferred in which X is a radical derived from an anion of a strong acid, for example of a hydrohalic or sulphonic acid. The reaction can also be promoted by converting the phenolic hydroxyl group of the compound (II) into a phenolate, for example, by reaction with a sodium alcoholate. The reaction of the two components is carried out in a solvent, for example, toluene, a xylene, methyl ethyl ketone or dimethyl formamide, preferably at an elevated temperature.

Examples of substituents Y in compounds of general formula (IV) which can be converted into a —COOR₃ group include the nitrile, carbaldehyde and hydroxymethyl groups.

A conversion of a substituent $R_3$ possibly to be carried out subsequently to the condensation can take place, for example, by saponification of a carboxylic acid ester ($R_3$ = alkyl) with a mineral acid or an alkali metal hydroxide in a polar solvent, for example water, methanol, ethanol, dioxan or acetone. The saponification is advantageously carried out with a strong base, such as sodium or potassium hydroxide, in a mixture of methanol and water, at ambient temperature or at a moderately elevated temperature. On the other hand, however, a carboxylic acid can also be esterified in the usual manner or an ester with a particular radical $R_3$ can be converted into one with a different radical $R_3$ by transesterification. The esterification of the carboxylic acids is preferably carried out in the presence of an acid catalyst, for example hydrochloric acid, sulphuric acid or p-toluenesulphonic acid, or a strongly acidic ion exchange resin. Transesterifications, on the other hand, require the addition of a small amount of a basic substance, for example of an alkali metal or alkaline earth metal hydroxide or of an alkali metal alcoholate.

For the preparation of salts with pharmacologically compatible organic or inorganic bases, for example, sodium hydroxide, potassium hydroxide, calcium hydroxide, ammonium hydroxide, methylglucamine, morpholine or ethanolamine, the carboxylic acids (I; $R_3$ = H) can be reacted with the appropriate bases. Mixtures of carboxylic acids with an appropriate alkali metal carbonate or bicarbonate can also be used.

The following Examples are given for the purpose of illustrating the present invention:

EXAMPLE 1

2-{4-[2-(3,5-Di-tert.-butyl-4-hydroxybenzoylamino)-ethyl]-phenoxy}-2-methylpropionic acid A mixture of 44.8 g. (0.25 mol) N-acetyl-tyramine, 69.5 g. (0.5 mol) anhydrous, powdered potassium carbonate and 750 ml. anhydrous butan-2-one is heated for 2 hours, while stirring at reflux temperature, and then 73.2 g. (0.375 mol) ethyl α-bromoisobutyrate and 1 g. potassium iodide are added thereto and the reaction mixture is again heated at reflux temperature.

After 40 hours and again after 70 hours boiling, in each case there are additionally added 35 g. potassium carbonate and 36.6 g. ethyl α-bromoisobutyrate. After a total reaction period of 130 hours, the reaction mixture is evaporated in a vacuum, poured into ice water and extracted with diethyl ether. The ethereal extract is washed 3 times with 0.5N aqueous sodium hydroxide solution, then with water and finally dried over anhydrous calcium chloride and evaporated. There are obtained 83.8 g. of an oily residue which still contains ethyl α-bromoisobutyrate. The oil is kept for 5 hours at 70° C. under a pressure of 0.1 mm. Hg and then cooled. The resultant crystalline slurry is washed with ligroin and dried. There are obtained 69.8 g. (95% of theory) of still not quite pure ethyl 2-[4-(2-acetaminoethyl)-phenoxy]-2-methylpropionate; m.p. 48°–51° C.

A solution of 119.1 g. (0.407 mol) ethyl 2-[4-(2-acetaminoethyl)-phenoxy]-2-methylpropionate in 750 ml. ethanol is mixed with a solution of 224.4 g. (4.00 mol) potassium hydroxide in 800 ml. water and heated under reflux for 8 hours. After cooling, exactly 4.00 mol hydrogen chloride, for example in the form of 2N hydrochloric acid, are added thereto, the mixture is more strongly cooled and, after some time, the precipitated crystals are filtered off with suction. These are washed with water and dried. There are obtained 48.4 g. (53% of theory) of product; m.p. 274° C. (decomp.). From the mother liquor, there are obtained, after distilling off the ethanol and cooling, a further 32.5 g. (36% of theory) of product; m.p. 263°–270° C. The crude 2-[4-(2-aminoethyl)-phenoxy]-2-methylpropionic acid thus obtained is recrystallized from ethanol-water (4:1 v/v) and then has a melting point of 284° C. The corresponding hydrochloride has a melting point of 187°–189° C.

A solution of 58 g.(0.26 mol) of this carboxylic acid in 600 ml. absolute ethanol is gasified with dry hydrogen chloride, while stirring and cooling with ice, from the surface until saturated. The reaction mixture is left to stand in a closed vessel for 12 hours. Subsequently, the ethanol and hydrogen chloride are removed in a vacuum. Water is added to the residue, followed by extracting 3 times with diethyl ether. The aqueous phase is rendered distinctly alkaline and then extracted 3 times with chloroform. The chloroform extract is washed with a little water, dried over anhydrous potassium carbonate and evaporated. By distillation of the residue, there are obtained, between 125 and 128° C./0.1 mm.Hg, 53.2 g. (82% of theory) colorless ethyl 2-[4-(2-aminoethyl)-phenoxy]-2-methylpropionate.

To a solution of 8.83 g. (35.2 mMol) ethyl 2-[4-(2-aminoethyl)-phenoxy]-2-methylpropionate in 75 ml. anhydrous pyridine is added dropwise at 5° C. 1.54 ml. (17.6 mMol) phosphorus trichloride. The reaction mixture is stirred for 30 minutes at 5° C., then 8.8 g. (35.2 mMol) 3,5-di-tert.-butyl-4-hydroxybenzoic acid introduced, followed by further stirring for 1 hour at 5° C., whereafter the reaction mixture is left to stand overnight at ambient temperature. Subsequently, the reaction mixture is heated for 30 minutes on a steambath, cooled and poured into ice-water. The mixture is acidified with concentrated hydrochloric acid and the precipitated material is taken up in ethyl acetate. The ethyl acetate phase is washed 3 times with 0.5N aqueous sodium hydroxide solution, once with 0.5N hydrochloric acid and then with water, thereafter dried and finally evaporated. The evaporation residue is recrystallized from an ethyl acetate-ligroin mixture to give 10.2 g. (60% of theory) ethyl 2-{4-[2-(3,5-di-tert.-butyl-4- hydroxybenzoylamino)-ethyl]-phenoxy} -2-methylpropionate; m.p. 132°–134° C.

A mixture of 11.3 g. (23.4 mMol) of this ethyl ester, 130 ml. methanol and 58.5 ml. (58.5 meq.) 1N aqueous potassium hydroxide solution is stirred for 2 hours at 40° C. 60 ml. 1N hydrochloric acid are then added dropwise thereto, solid material is filtered off with suction and the filter cake is washed with water, dried and recrystallized from an ethyl acetate-ligroin mixture. There are thus obtained 8.1 g. (76% of theory) 2-{4-[2-(3,5-di-tert.-butyl-4-hydroxy-benzoylamino)-ethyl]-phenoxy}-2-methylpropionic acid; m.p. 200°–202° C.

The N-acetyl-tyramine used as starting material can be prepared by one of the two following methods:

1. 64.0 g. (0.466 mMol) tyramine are mixed, while stirring, with 200 ml. acetic anhydride, a clear solution thereby being formed, with spontaneous heating up. This solution is seeded with a few crystals of N-acetyl-tyramine, whereafter crystallization occurs immediately. The reaction mixture is rapidly cooled, filtered with suction, washed with diethyl ether and water and dried. There are obtained 59 g. (71% of theory) N-acetyl-tyramine with a melting point of 126° C. By evaporation of the mother liquor, dissolving the residue in dilute aqueous sodium hydroxide solution, filtration and acidification of the filtrate, there are obtained a further 5.5 g. (6% of theory) of N-acetyl-tyramine with a melting point of 122°–124° C. After recrystallization from ethyl acetate, the N-acetyl-tyramine melts at 129°–131° C.

2. To a solution of 54.9 g. (0.4 mol) tyramine in 200 ml. pyridine are added dropwise, while stirring at 30°–35° C., 65.8 g. (0.84 mol) acetyl chloride. The reaction mixture is subsequently heated for 15 minutes on a boiling water-bath, then cooled and poured into an ice-water mixture. By the addition of concentrated hydrochloric acid, the mixture is rendered distinctly acidic and subsequently extracted with chloroform. The chloroform phase is washed with water, dried over anhydrous calcium chloride and then evaporated. As residue, there are obtained 88.5 g. (quantitative yield) diacetyl-tyramine with melting point of 99°–100° C., after recrystallization from benzene. The diacetyl-tyramine is now dissolved in 500 ml. methanol. 800 ml. (0.8 mol) 1N aqueous potassium hydroxide solution are then added dropwise, the temperature thereby increasing to about 30° C., and the reaction mixture subsequently maintained for 2 hours at an internal temperature of 50° C. The mixture is thereafter cooled, weakly acidified with concentrated hydrochloric acid and the methanol evaporated off in a vacuum. The product which crystallizes out is filtered off with suction, thoroughly washed with water and then dried. There are obtained 58.3 g. (81% of theory) N-acetyl-tyramine which, after recrystallization from ethyl acetate, melts at 131° C.

EXAMPLE 2

2-{4-[3-(3,5-Di-tert.-butyl-4-hydroxyphenyl)-propionylamino]-ethyl)-phenoxy}-2-methylpropionic acid In a manner analogous to that described in Example 1, by the condensation of 3-(3,5-di-tert.-butyl-4-hydroxyphenyl)-propionic acid with ethyl 2-[4-2-aminoethyl)-phenoxy]-2-methylpropionate in the presence of phosphorus trichloride, there is obtained, in a yield of 91% of theory, crude ethyl 2-{4-(2-[3-(3,5-di-tert.-butyl-4-hydroxyphenyl)-propionylamino]-ethyl)-phenoxy }-2-methylpropionate in the form of a colorless oil and from this, by hydrolysis at 30° C., 2-{4-(2[3-(3,5-di-tert.-butyl-4-hydroxyphenyl)-propionylamino]-ethyl)-phenoxy }-2-methylpropionic acid in a yield of 55% of theory which, after recrystallization from an ethyl acetate-ligroin mixture, melts at 168°–171° C.

The above-mentioned acid can also be prepared by the hydrolysis of the methyl ester which melts at 105°–107° C., after recrystallization from ethyl acetate-ligroin. The methyl ester can be prepared, in a manner analogous to that described in Example 1, by the condensation of 3-(3,5-di-tert.-butyl-4-hydroxyphenyl)-propionic acid with methyl 2-[4-(2-aminoethyl)-phenoxy]-2-methylpropionate in the presence of phosphorus trichloride.

EXAMPLE 3

2-{4-(2-[3-(3,5-Di-tert.-butyl-4-hydroxyphenyl-propionylamino]-ethyl)-phenoxy}-2-methylpropionic acid.

A mixture of 50 g. (0.18 mol) 3-(3,5-di-tert.-butyl-4-hydroxyphenyl)-propionic acid, 24.6 g. (0.18 mol) tyramine and 150 ml. xylene is heated for 72 hours under a water separator at reflux temperature and subsequently evaporated in a vacuum. As residue, there are obtained 68.0 g. (95% of theory) N-[2-(4-hydroxyphenyl)-ethyl]-3-(3,5-di-tert.-butyl-4-hydroxyphenyl)propionamide which, after recrystallization from ethyl acetate-ligroin, melts at 139°–141° C.

68 g. (0.171 mol) of this amide are heated with 47.5 g. (0.342 mol) potassium carbonate in 2.5 liters butan-2-one for 2 hours at reflux temperature, then mixed with 50 g. (0.256 mol) ethyl 2-bromo-2-methylpropionate and 5 g. potassium iodide and again heated to reflux temperature. After 24 hours and 48 hours, there are again added 24.8 g. (0.128 mol) ethyl 2-bromo-2-methylpropionate and 23.7 g. (0.171 mol) potassium carbonate. After a total reaction period of 120 hours, the precipitate is filtered off with suction, washed with acetone and the combined filtrates evaporated. There are obtained 112 g. of an oily residue which still contains ethyl 2-bromo-2-methylpropionate. The oil is maintained for 5 hours at 70° C. under vacuum of 0.1 mm.Hg and then cooled. There is obtained a quantitative yield of crude ethyl 2 {4-(2-[3-(3,5-di-tert.-butyl-4-hydroxyphenyl)-propionylamino]-ethyl)-phenoxy }-2-methylpropionate in the form of a colorless oil.

In a manner analogous to that described in Example 1, from this ester there is obtained, by hydrolysis at 30° C., 2-{4-(2-[3-(3,5-di-tert.-butyl-4-hydroxyphenyl)-propionylamino]-ethyl)-phenoxy }-2-methylpropionic acid in a yield of 51% of theory. After recrystallization from ethyl acetate-ligroin, the compound has a melting point of 168°–171° C.

EXAMPLE 4

In a manner analogous to that described in Example 1, by the reaction of ethyl 2-[4-(2-aminoethyl)-phenoxy]-2-methylpropionate in the presence of phosphorus trichloride with the appropriate acids, there are obtained the following compounds:

(a) ethyl 2-{4-[2-(3,5-di-tert.-butyl-4-hydroxyphenylacetamino)-ethyl]-phenoxy}-2-methylpropionate; m.p. 100°–100.5° C., after recrystallization from diethyl ether; yield 67% of theory; and from this, by hydrolysis, 2-{4-[2-(3,5-di-tert.-butyl-4-hydroxyphenylacetamino)-ethyl]-phenoxy{-2-methylpropionic acid; m.p. of the sodium salt 214° C. (decomp.); yield 84% of theory.

(b) ethyl 2-{4-[2-(3,5-di-tert.-butyl-4-hydroxyphenyl-α-methylacetamino)-ethyl]-phenoxy}-2-methylpropionate; m.p. 118°-120° C., after recrystallization from ethyl acetate-ligroin; yield 88% of theory; and from this, by hydrolysis, 2-{4-[2-(3,5-di-tert.-butyl-4-hydroxyphenyl-α-methylacetamino)-ethyl]-phenoxy}-2-methylpropionic acid; m.p. 80°-83° C., after recrystallization from ethyl acetate/ligroin; yield 50% of theory.

(c) ethyl 2-{4-[2-(3,5-di-tert.-butyl-4-hydroxyphenyl-α,α-dimethylacetamino)-ethyl]-phenoxy}-2-methylpropionate; colorless, viscous oil; yield 41 % of theory; and from this, by hydrolysis, 2-{4-[2-(3,5-di-tert.-butyl-4-hydroxyphenyl-α,α-dimethylacetamino)-ethyl]-phenoxy}-2-methylpropionic acid.

(d) ethyl 2-{4-[2-{3-(3,5-di-tert.-butyl-4-hydroxyphenyl)-acryloylamino}-ethyl]-phenoxy}-2-methylpropionate; m.p. 58°-64° C. (solid foam); yield 88% of theory, and from this, by hydrolysis, 2-{4-[2-{3-(3,5-di-tert.-butyl-4-hydroxhphenyl)-acryloylamino}-ethyl]-phenoxy}-2-methylpropionic acid; m.p. 210.5°-211° C., after recrystallization from acetone; yield 87% of theory.

(e) ethyl 2-{4-[3-(3,5-di-tert.-butyl-4-hydroxyphenyl)-propionylaminomethyl]-phenoxy}-2-methylpropionate; pure oil $n_D^{20}$ = 1.5320; yield 72% of theory, and from this, by hydrolysis, 2-{4-[3-(3,5-di-tert.-butyl-4-hydroxyphenyl)-propionylaminomethyl]-phenoxy}-2-methylpropionic acid; m.p. 189° C., after recrystallization from methanol; yield 75% of theory.

EXAMPLE 5

In a manner analogous to that described in Example 1, by the reaction of 4-(2-aminoethyl)-phenoxyacetic acid in the presence of phosphorus trichloride with the appropriate acids, there are obtained the following compounds:

(a) ethyl 2-{4-[2-(3,5-di-tert.-butyl-4-hydroxybenzoylamino)-ethyl]-phenoxy}-acetate; m.p. 129°-129.5° C., after recrystallization from isopropanol; yield 70% of theory; and from this, by hydrolysis, 2-{4-[2-(3,5-di-tert.-butyl-4-hydroxybenzoylamino)-ethyl]-phenoxy}-acetic acid; m.p. 209°-210° C., after recrystallization from isopropanol/water; yield 55% of theory.

(b) ethyl 2-{4-[2-{3-(3,5-di-tert.-butyl-4-hydroxyphenyl)-propionylamino}-ethyl]-phenoxy}-acetate; colorless, very viscous oil $n_D^{20}$ = 1.5390; yield 84% of theory; and from this, by hydrolysis, 2-{4-[2-{3-(3,5-di-tert.-butyl-4-hydroxyphenyl)-propionylamino}-ethyl]-phenoxy}-acetic acid; m.p. of the sodium salt 190° C. (decomp.); yield 75% of theory.

The ability of the instant compounds to lower the serum lipid level and the cholesterol level as well as their activity as thrombocyte aggregation inhibiting agents are demonstrated by the following illustrative experiments:

Experiment A

The test compounds were administered orally to male rats of a weight of about 200 g (10 animals per substance in each case) in the dosages listed below. The treatment continued for 7 days. On the seventh day the animals were killed by neck blow and bled white. The concentration of the triglycerides and the cholesterol in the serum of the animals was then determined enzymatically. The control animals were given carrier substances without test compound. The results, expressed as percent reduction as compared to the control animals, are set forth in the following Table:

TABLE

| Test Compound | Prep. Example No. | Dosage in mg/kg | Reduction in % Triglycerides | Cholesterol |
|---|---|---|---|---|
| 2-{4-[2-(3,5-di-tert.-butyl-4-hydroxybenzoylamino)-ethyl]-phenoxy}-acetic acid | 5 (a) | 25 | 24 | — |
| 2-{4-[2-(3,5-di-tert.-butyl-4-hydroxyphenyl-α-methylacetamino)-ethyl]-phenoxy}-2-methylpropionic acid | 4 (b) | 25 | 49 | 21 |
| 2-{4-[2-{3-(3,5-di-tert.-butyl-4-hydroxyphenyl)-acryloylamino}-ethyl]-phenoxy}-2-methylpropionic acid | 4 (d) | 50 | 13 | — |
|  |  | 100 | 21 | — |
| 2-{4-[2-(3,5-di-tert.-butyl-4-hydroxyphenylacetamino)-ethyl]-phenoxy}-2-methylpropionic acid | 4 (a) | 25 | 0 | 6 |
| 2-{4-[3-(3,5-di-tert.-butyl-4-hydroxyphenyl)-propionylaminomethyl]-phenoxy}-2-methylpropionic acid | 4 (e) | 25 | 27 | 3 |
| 2-{4-(2-[3-(3,5-di-tert.-butyl-4-hydroxyphenyl)-propionylamino]-ethyl)-phenoxy}-2-methylpropionic acid | 2 | 5 | 49 | 5 |
|  |  | 12.5 | 43 | 12 |
|  |  | 25 | 43 | 20 |
|  |  | 50 | 49 | 30 |

Experiment B

In this experiment arachidonic acid was administered intravenously to male rabbits in a dosage of 1.4 mg/kg. One group of 5 rabbits was used as a control group and a second group was used as the test group. Two hours before injection of the arachidonic acid the test group was pre-treated with 2-{4-(2-[3-(3,5-di-tert.-butyl-4-hydroxyphenyl)-propionylamino]-ethyl)-phenoxy}-2-methylpropionic acid in dosages of 10 mg/kg and 20 mg/kg.

Immediately after injection of the arachidonic acid in the stated dosage range, death of the control animals occurred, as described by Silver et al (Sci. 183, 1974, 1085). By pre-treatment of the test animals with the inventive compound a survival rate of 100% could be demonstrated even at the lower test dosage of 10 mg/kg.

The novel compounds may be administered by themselves or in conjunction with carriers which are pharmacologically acceptable, either active or inert. The dosage units are similar to those of the heretofore known anti-cholesterol agents, e.g., about 1 to 2 grams per day for an adult or about 30 mg/kg per day although higher or lower dosages can be used. Rather than a single dose it is preferable if the compounds are administered in the course of a day, i.e., about four applications of 500 mg. each at spaced time intervals or 8 of about 250 mg. each. A convenient form of administration is in a gelatin capsule.

For the preparation of pharmaceutical compositions, the new compounds according to the present invention are mixed in the usual manner with appropriate pharmaceutical diluents or carriers, arome, flavoring and coloring materials and formed, for example, into tablets or dragees or, with the addition of appropriate adjuvants, suspended or dissolved in water or in an oil, for example olive oil.

The new compounds according to the present invention can be administered orally or parenterally in admixture with solid or liquid pharmaceutical diluents or carriers. As injection medium, it is preferred to use water which contains the stabilizing agents, solubilizing agents and/or buffers conventionally used in injection solutions. Additives of this kind include, for example, tartrate and borate buffers, ethanol, dimethyl sulphoxide, complex-forming agents (such as ethylenediaminetetraacetic acid), high molecular weight polymers (such as liquid polyethylene oxide) for viscosity regulation and polyethylene derivatives of sorbitan anhydrides.

Solid carrier materials include, for example, starch, lactose, mannitol, methyl, cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

It will be appreciated that the instant specification and examples are set forth by way of illustration and not limitation, and that various modifications and changes may be made without departing from the spirit and scope of the present invention.

What is claimed is:

1. Phenoxyalkylcarboxylic acid compound of the formula:

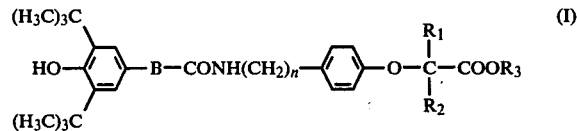

wherein
B is a valency bond or a straight-chained or branched, saturated or unsaturated hydrocarbon radical containing up to 3 carbon atoms;
n is 1 or 2 and
$R_1$, $R_2$ and $R_3$, which can be the same or different, are hydrogen atoms or lower alkyl; and the pharmacologically compatible salts thereof.

2. Phenoxyalkylcarboxylic acid compound as claimed in claim 1 wherein B is a valency bond.

3. Phenoxyalkylcarboxylic acid compound as claimed in claim 1 wherein B is a hydrocarbon radical of up to 3 carbon atoms.

4. Phenoxyalkylcarboxylic acid compound as claimed in claim 1 wherein B is alkylene of up to 3 carbon atoms.

5. Phenoxyalkylcarboxylic acid compound as claimed in claim 1 wherein B is alkenylene of up to 3 carbon atoms.

6. Phenoxyalkylcarboxylic acid compound as claimed in claim 1 wherein n is 1.

7. Phenoxyalkylcarboxylic acid compound as claimed in claim 1 wherein n is 2.

8. Phenoxyalkylcarboxylic acid compound as claimed in claim 1 wherein at least one of $R_1$, $R_2$ and $R_3$ is hydrogen.

9. Phenoxyalkylcarboxylic acid compound as claimed in claim 1 wherein at least one of $R_1$, $R_2$ and $R_3$ is lower alkyl.

10. Phenoxyalkylcarboxylic acid compound as claimed in claim 1 designated 2-{4-(2-[3-(3,5-di-tert.-butyl-4-hydroxyphenyl)-propionylamino]-ethyl)-phenoxy}-2-methylpropionic acid.

11. Phenoxyalkylcarboxylic acid compound as claimed in claim 1 designated 2-{4-[2-(3,5-di-tert.-butyl-4-hydroxyphenyl-α-methylacetamino)-ethyl]-phenoxy}-2-methylpropionic acid.

12. Phenylalkylcarboxylic acid compound as claimed in claim 1 designated 2-{4-[2-{3-(3,5-di-tert.-butyl-4-hydroxyphenyl)-acryloylamino}-ethyl]-phenoxy}-2-methylpropionic acid.

13. Phenylalkylcarboxylic acid compound as claimed in claim 1 designated 2-{4-[3-(3,5-di-tert.-butyl-4-hydroxyphenyl)-propionylaminomethyl]-phenoxy}-2-methylpropionic acid.

14. Phenylalkylcarboxylic acid compound as claimed in claim 1 designated 2-{4-[2-(3,5-di-tert.-butyl-4-hydroxybenzoylamino)-ethyl]-phenoxy}-acetic acid.

15. Therapeutic compositions for lowering the serum lipid and/or cholesterol level and for inhibiting thrombocyte aggregation in mammals comprising a pharmocologically acceptable carrier and, in therapeutically effective amounts, a phenoxyalkylcarboxylic acid compound as claimed in claim 1.

16. Method for lowering the serum lipid and/or cholesterol level and for inhibiting thrombocyte aggregation in mammals which method comprises administering thereto an effective amount of a phenoxyalkylcarboxylic acid compound as claimed in claim 1.

17. Method as claimed in claim 16 wherein said compound is applied at a dosage of about 30 mg/kg per day.

18. Method as claimed in claim 16 wherein said compound is at least one selected from the group consisting of:
2-{4-(2-[3-(3,5-di-tert.-butyl-4-hydroxyphenyl)-propionylamino]-ethyl)-phenoxy}-2-methylpropionic acid
2-{4-[2-(3,5-di-tert.-butyl-4-hydroxyphenyl-α-methylacetamino)-ethyl]-phenoxy}-2-methylpropionic acid
2-{4-[2-{3-(3,5-di-tert.-butyl-4-hydroxyphenyl)-acryloylamino}-ethyl]-phenoxy}-2-methylpropionic acid
2-{4-[3-(3,5-di-tert.-butyl-4-hydroxyphenyl)-propionylaminomethyl]-phenoxy}-2-methylpropionic acid
2-{4-[2-(3,5-di-tert.-butyl-4-hydroxybenzoylamino)-ethyl]-phenoxy}-acetic acid.

* * * * *